(12) United States Patent
Norén

(10) Patent No.: US 6,669,969 B2
(45) Date of Patent: Dec. 30, 2003

(54) PESTICIDAL USE OF A PARASITIC FLAGELLATE FOR ELIMINATING OR SUPPRESSING HARMFUL ALGAE BLOOMS

(76) Inventor: Fredrik Norén, S-453 30, Lysekil (SE)

( * ) Notice: Subject to any disclaimer, the term of this patent is extended or adjusted under 35 U.S.C. 154(b) by 122 days.

(21) Appl. No.: 09/921,174

(22) Filed: Aug. 2, 2001

(65) Prior Publication Data

US 2002/0029393 A1 Mar. 7, 2002

Related U.S. Application Data

(63) Continuation of application No. PCT/SE00/00170, filed on Jan. 28, 2000.

(30) Foreign Application Priority Data

Feb. 3, 1999 (SE) ................................................ 9900364

(51) Int. Cl.[7] ........................ A01N 63/00; A61K 35/80; A61K 35/84
(52) U.S. Cl. ............. 424/780; 424/195.15; 424/195.17; 435/243; 435/257.1; 435/258.1
(58) Field of Search ............................... 424/780, 93.1, 424/405, 195.15, 195.17; 435/325, 243, 257.1, 258.1, 260, 254.1

(56) References Cited

PUBLICATIONS

"Parasitism of Photosynthetic Dinoflagellates in a Shallow Subestuary of Chesapeake Bay, USA"; by Coats et al., Smithsonian Environmental Research Center, P.O. Box 28, Edgewater, Maryland 21037, USA; Aquatic Microbial Ecology; vol. 11: 1–9, 1996.

"Parvilucifera infectans Noren et Moestrup gen. et sp. nov. (Perdinsozoa phylum nov.): a Parasitic Flagellate Capable of Killing toxic Microalgae"; Noren et al., European Journal of Protistology; 35, 233–254; Oct. 15, 1999.

Primary Examiner—Leon B. Lankford, Jr.
Assistant Examiner—Ruth A. Davis
(74) Attorney, Agent, or Firm—Samuels, Gauthier & Stevens, LLP

(57) ABSTRACT

The present invention related to *Parvilucifera infectans*, a new parasitic organism described by Noren and Moestrup (in prep. "*Parvilucifera infectans*, gen. et. spec.nov. A parasitic dinoflagellate infecting thecate dinoflagellates.") capable of infecting and killing several toxic or potentially harmful dinoflagellates, method for infecting toxin producing dinoflagellates, and method for propagating *P. infectans*.

10 Claims, 2 Drawing Sheets

Figure 1:
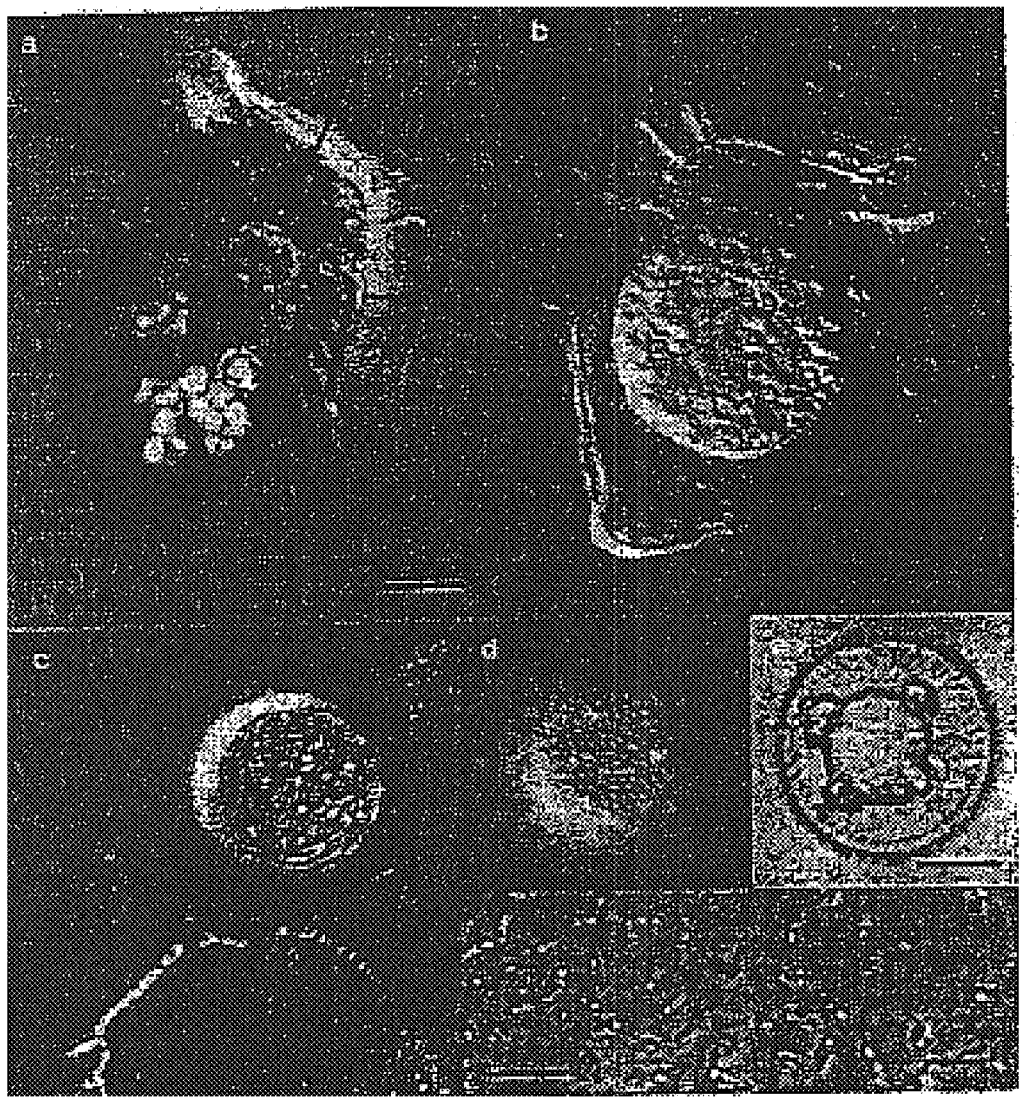

PESTICIDAL USE OF A PARASITIC FLAGELLATE FOR ELIMINATING OR SUPPRESSING HARMFUL ALGAE BLOOMS

This is a continuation of copending application(s) International Application PCT/SE00/00170 filed on Jan. 28, 2000 and which designated the U.S.

TECHNICAL FIELD

The present invention relates to a parasitic microorganism being able to kill dinoflagellates, a method for eliminating or suppressing growth and/or replication of harmful dinoflagellates of, e.g., the genuses Dinophysis, and Alexandrium, method for propagating said microorgansm, and a composition containing said microorganism for carrying out said method.

The object of the present invention is to obtain a possibility of eliminating poisonous or otherwise harmful dinoflagellates from the sea, thereby avoiding accumulation of dinoflagellate related toxins in shellfish, such as mussels and oysters.

BACKGROUND OF THE INVENTION

Most coastal waters are even so often invaded by harmful microalgae blooms. Certain toxic algae will kill wild and farmed fish, and particularly the latter suffers, as it can not escape from the algae in contrast to the wild ones. This will cause an immediate economical impact on the breeders of farmed fish, as all stages of the farmed fish will be killed, and several years production will be affected. Other algae produce potent toxins that accumulate in filter-feeding shellfish and poison human consumers. Thus marketing and sale of such shellfish from such affected coastal areas is forbidden for long periods.

Bloom of microalgae is further harmful as the algae when dead will consume most of the oxygen present in the water, thereby causing bottom fauna death, and/or fish flight.

Toxic marine dinoflagellates can cause shellfish, e.g. mussels and oysters, to accumulate toxins in such concentrations that they become dangerous as human food. Toxic dinoflagellates can cause different types of shellfish poisoning; DSP (Diarrhetic Shellfish Poisoning, caused by members of the genuses Dinophysis and Prorocentrum), PSP (Paralytic Shellfish Poisoning, caused by the genuses Alexandrium, Gymnodinium, and Pyrodinium) and NSP (Neurotoxic Shellfish Poisoning, caused by the genus *Gymnodinium breve*). Those intoxifications of the mussels inhibits the mussel industry as the mussels can not be harvested for shorter or longer periods. This production loss of the shellfish industry is estimated to 1–2 billions USD yearly. A further very important aspect is also that those who harvest shellfish for food consumption, have no possibility to check for high toxin content in the mussels. The shellfish industry has grown much during the last decades and is expected to grow even more due to the need of food for a growing human population. The aqua culture and shellfish market is expanding but is also suffering from marine pests, such as toxic marine phytoplankton.

A marine microalgae bloom is widely defined when the water is discoloured and/or comprises a cell concentration of $1 \times 10^6$ cells per liter. The recording of those blooms is ancient but it is only in modern time we have been aware of the problems and suffer to a larger extent therefrom. It is also suspected that human eutrofication is causing the more intense and more frequently occurring blooms. The algae species that are producing toxins and are capable of forming blooms are mostly belonging to the dinoflagellate group of organisms.

In some Spanish fjords mussel harvesting sites have been closed down up to a half year. This could, hopefully be shortened down to some weeks, if a regulatory parasite to the toxic dinoflagellates is found.

Thus scientists are struggling to find methods to control those harmful microalgae blooms and are intensifying the efforts to find such methods (D. A. Anderson, *Nature*, 388:513–514, August, 1997).

At present the best method is to spread huge amounts of clay into the water in order to clog the phytoplankton and hence rapidly precipitating them out of the water column (corresponding to the flocculation method in industrial sewage and waste water treatment). This is, however, a very costly method and labour intensive. The method has only been applied in the republic of China (D. A. Anderson, *Nature*, 388:513–514, August, 1997).

JP patent specification 6001701 discloses red tide controlling material comprising a fibrous material carrier supporting a highly unsaturated fatty acid, whereby the material is supposed to kill the red tide plankton in contact therewith.

JP patent specification 5169088 discloses use of an attack bacteria of red tide plankton inhibitor comprising bentonite or kaolin-based clay-like particles.

JP patent specification 6016504 discloses a surfactant composition for controlling red tide, which surfactant composition comprises polyoxyalkylene alkyl ether, polyalkylene glycol fatty acid ester, polyoxyalkylene fatty acid amide, and polyoxyalkylene alkyl amine, which composition is sprayed onto the red tide plankton.

JP patent specification 8289693 discloses the use of radioactive compounds for killing red tide plankton.

F. J. R. Taylor, *J. Fish. Res. Bd. Canada*, 25(10) :2241–2245 (1968) discusses the parasitism of toxin-producing dinoflagellate *Gonyaulax catenella* by the endoparasitic dinoflagellate *Amoebophyra ceratii*, and concludes that it seems possible that the answer to harmful plankton blooms is the use of a biological control agent, similar to *A. ceratii*, as *A. ceratti* was not totally fatal to the host population in the case investigated.

Elbrächer, M. et al, in "Physiological Ecology of Harmful Algal Blooms", D. M. Anderson, A. D. Cembella & G. M. Hallegraeff, eds. Springer-Verlag Berlin Heidelberg, pp 351–363 (1998) discuss parasites of harmful algae as a tool for preventing harmful microalgael blooms. In this article the use of *A. ceratii* as proposed by Taylor, supra, seems to have been dismissed by Nishitani, L. et al, in "Toxic Dinoflagellates", D. M. Anderson et al, eds, Elsevier Sci. Publ. Co. New York, N.Y. pp 225–230 (1985).

Coats, D. W. et al., *Aquat. Microb. Ecol.*, 11:1–9, (1996) discuss parasitism of photosynthetic dinoflagellates in a shallow subestuary of Chesapeake Bay, USA. I. a. Coats et al discuss the parasitism of *A. ceratii* on Alexandrium (=*Gonyaulax*) *catenella* according to Taylor, supra, and the dismissal of Nishitani et al, supra, and are of the opinion that the Taylor's suggestion should be reexamined.

Scientists have been searching for a natural method of controlling these blooms and the use of some kind of parasitic organism or predator has been in mind and requested since parasites have been found to be an important regulating factor of a microalgae bloom. (Coats et al, supra). However, until today no such organism has been found that sucessfully is inhibiting a toxic, or otherwise harmful bloom, or could be industrially multiplied into an effective bloom inhibitor.

One parasite known to infect the toxic dinoflagellate genus Dinophysis is the parasitic dinoflagellate *Amoe-* bophrya ceratii (Taylor et al, supra). It is able to infect Dinophysis but is not able to graze down a bloom of the same species. (Coats et al, supra). This parasite has neither been actively used in attempts to control a dinoflagellate bloom, i.e. it has not been artificially cultured and reinserted in the natural environment as a pest controlling agent.

Thus the only in vivo method today, for terminating marine microalgae blooms is to put large amounts of clay into the sea to obtain a flocculation and precipitation of the algae. An intense research for biological controllers of the marine algae blooms is ongoing but today no such organism is known to work efficiently or is available to give an efficient control of the blooms. (Elbrächer et al, supra). The parasitic dinoflagellate Amoebophrya ceratii is able to infect Dinophysis sp. but is not able to control a bloom of the same species. Amoebophrya ceratii has neither been used to actively control a bloom of dinoflagellates.

DESCRIPTION OF THE PRESENT INVENTION

It has, however, now surprisingly been found possible to solve this problem as a new parasitic organism has been found and isolated that is a lethal parasite to toxic and otherwise harmful dinoflagellates and more efficient than the previously known Amoebophrya ceratii. This new organism, hereinafter named Parvilucifera infectans, abbreviated Parvilucifera infectans, is described by Norén and Moestrup (Norén, F. et. al. Europ. J. Protistol. 35:233–254 (1999) "Parvilucifera infectans Norén et Mostrup gen. et. spec. nov. (Perkinsozoa phylum nov.); a Parasitic Flagellate Capable of Killing Toxic Microalgae").

FIG. 1 shows infection of Parvilucifera infectans in Dinophysis. Scale bars=10 μm.
  a. Early infection—1 day in living specimen of Dinophysis. The arrow denotes Parvilucifera infectans.
  b. Late infection—2 days, Dinophysis host is dead.
  c. Release of Parvilucifera infectans sporangium from Dinophysis
  d. Papillar surface structure of Parvilucifera infectans
  e. Restbody formation in sporangium of Parvilucifera infectans after release of zoides
  f. Zoides of Parvilucifera infectans.

Figure 2:
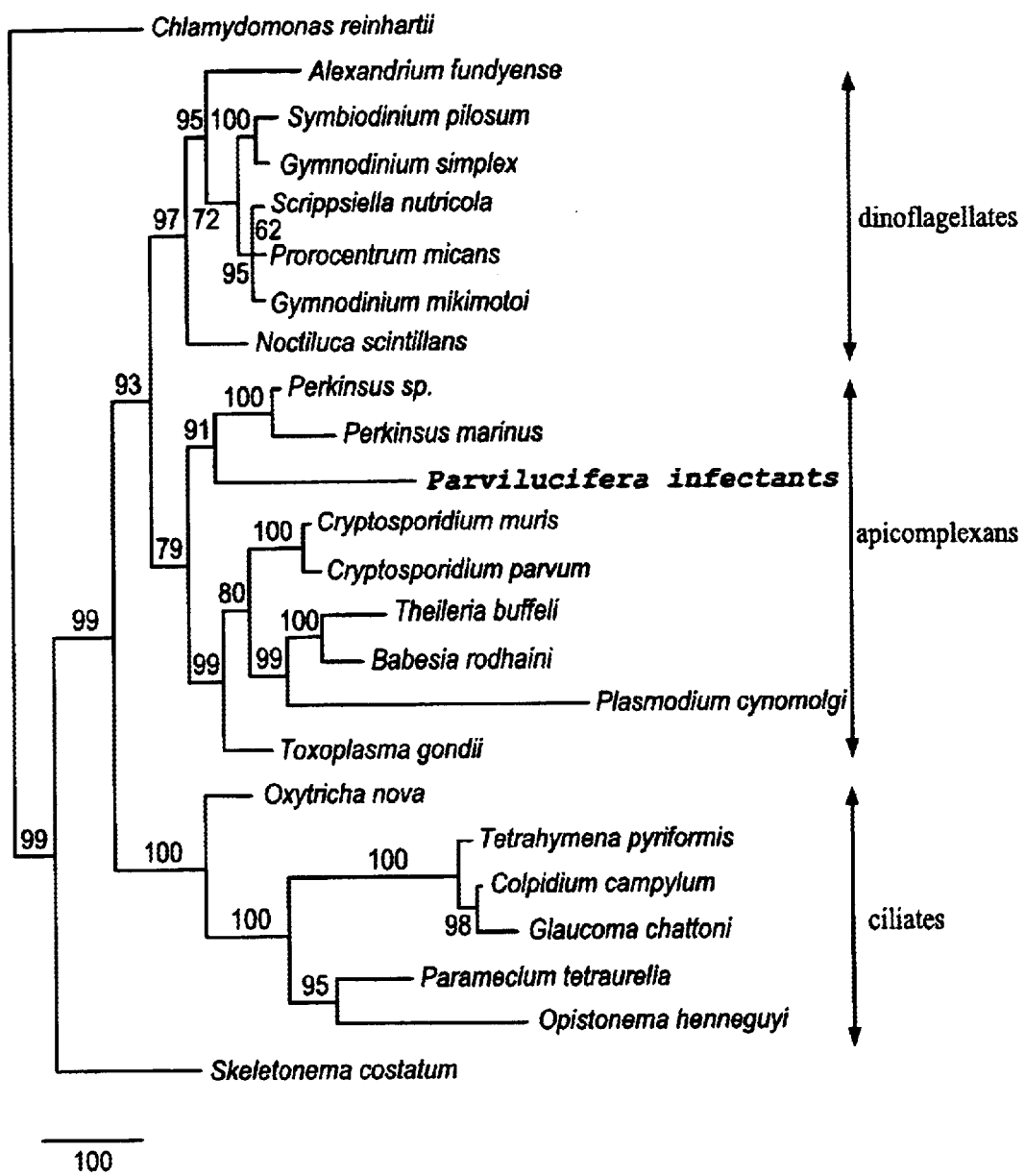

FIG. 2 shows the taxonomic tree for Parvilucifera infectans

Parvilucifera infectans has been deposited at the Culture Collection of Algae and Protozoa on the 4th day of December, 1998, under the deposition number CCAP No. 2060/1.

Parvilucifera infectans is naturally, but very sparsely occurring at the Swedish west coast.

Berland, B. R. et al., Aquatic Microbial Ecology, 9:183–189 (1997) observed an organism that might have been Parvilucifera infectans. However, the observation was lacking proper identification to provide for a guaranteed discovery. They were also explicitly stating that the organism found, was not a parasitic organism, but a sexual phase of Dinophysis. This has been proven to be false by Norén and Moestrup (supra) in their study of the organism.

The method to inhibit blooms of harmful plankton algae is straight forward: It is possible to maintain Parvilucifera infectant in culture and to multiply it in large amounts. This can be scaled up in industrial production to yield large amounts of Parvilucifera infectans. These cultured Parvilucifera infectans are then spread over areas where a bloom of toxic dinoflagellates, susceptible for infection by Parvilucifera infectans, occurs and causes a threat to human activities. Parvilucifera infectans is used as an infection inoculum (a seed) and hence is speeding up an optional natural process within a much shorter time period than is the case in a natural process.

Until today no one has been able to culture the causative parasite or to determine the ecological parameters leading to a regulation of a phytoplankton bloom using parasites. By using Parvilucifera infectans in waters having an ongoing harmful dinoflagellate bloom, consisting of dinoflagellates being susceptible to infection by Parvilucifera infectans, the toxic species could be regulated in abundance and a non-toxic plankton community could be established in much shorter time period.

Five sporangia of Parvilucifera infectans, are able to infect and kill a population of 20,000 cells of Dinophysis sp. within three days and thereafter to produce a cascade of new parasites. This process has also been repeated with Alexandrium fundyense, Alexandrium ostenfeldii, Alexandrium tamarense, Alexandrium anderssonii, Alexandrium catenella, Gymnodium sanguineum, Peridinium faeroensis= Pentapharsodinium dalei, (all species in this document are named and described according to "Identifying Marine Phytoplankton", Tomas C. R. Ed. 1997 Academic Press).

The life cycle of the Parvilucifera infectans comprises, as for as known, of a zoide stage that is a small flagellated zoide (3.5 μm in length) which is infecting the host cell and thereafter develops into a sporangium stage having a diameter of 20 to 100 μm and comprising 500–2000 new zoides. During this latter stage the dinoflagellate host cell is gradually degraded and finally killed which takes between 1 to 2 days from infection. After the death of the host cell the new sporangium is released into the water and the sporangium is able to release the zoides and start a new infection cycle. The sporangium is also able to persist in a dormant stage (resting stage) and the survival of the resting stage is enhanced by lowering the temperature and to keep the cells out of the vicinity of potential host cells.

Parvilucifera infectans is up to date known to infect members of the genuses Dinophysis, Alexandrium, Protoperidinium, Diplopsalis, Ceratium, Prorocentrum, Gymnodinium, and Gyrodinium. Dinophysis comprises the toxic species D. acuta, D. norvegica, D. dens, and D. acuminata which all are infested and killed by Parvilucifera infectans. Alexandrium comprises the toxic species A. tamarense, A. ostenfeldii, and A. fundyense which all are infected and killed by Parvilucifera infectans. Prorocentrum comprises the toxic Prorocentrum lima and the bloom forming species Prorocentrum micans which both are infected and killed by Parvilucifera infectans.

The method to inhibit blooms of harmful microalgae comprises at least two parts, viz
  i. the method of culturing Parvilucifera infectans to yield pure large quantities of Parvilucifera infectans, and
  ii. the method of adding Parvilucifera infectans into marine and limnic environments to enhance the extinction of a harmful microalgae bloom or a microalgae bloom that is causing nuisance.

Propagation

A. Sporangia of Parvilucifera infectans are added to a monoculture of dinoflagellates susceptible to infection by Parvilucifera infectans. The dinoflagellate culture should be maintained at optimal condition for the specific species as specified by culture collecting centres, and by common practise known to the one skilled in the art. The temperature should exceed 15° C. in order to obtain rapid infection.

Three alternatives to collect Parvilucifera infectans are thereby possible;

i. Have a running culture of dinoflagellates, adding continuously new cultured dinoflagellates into the vessel comprising *Parvilucifera infectans* and collecting sporangia, and/or infected dinoflagellates continuously from the bottom of the culturing vessel.

ii. Have a batch culture of dinoflagellates, susceptible to infestation by *Palvilucifera infectans*, and to add *Parvilucifera infectans*. When the infection is completed the bottom water of a vessel is collected where all of the new produced *Parvilucifera infectans* will be present.

iii. Taking natural water from the microalgal blooming area into a batch culture and add *Parvilucifera infectans* thereto. After the batch has been extensively infected with *Parvilucifera infectans*, the water is returned to the bloom area as an infection inoculum.

After treatment i. or ii. the collected *Parvilucifera infectans* is placed dark and in low temperature, +5° C. to +8° C. *Parvilucifera infectans* will go into a dormitory stage and optional living specimens of the host dinoflagellate will die. When a pure *Parvilucifera infectans* population is obtained, antibacterial action can be taken as a treatment of the water with an antibiotic or other antibacterial agents.

The final product, i.e. a water having a high concentration of *Parvilucifera infectans* can be stored for long time at +5° C. and in darkness. Hereby, the water can be cryopreservated in order to store the *Parvilucifera infectans* before use. *Parvilucifera infectans* can also be stored by dry-preservation.

B. The use of culturing media to culture *Parvilucifera infectans*. The closest phylogenetical relative is the family Perkinsidae (phylum apicomplexa) which can be cultured using fluid thioglycollate medium.

II. The aqueous solution comprising the *Parvilucifera infectans* sporangium is spread over a water containing a dinoflagellate of the above genus, e.g.; by spraying from an aircraft, spraying using a water canon from a boat, or distribution from a long tube comprising evenly distributed nozzles, which tube is arranged perpendicular to the longitudinal axis of a boat.

According to the present invention a concentration of 1000 sporangia comprising at least 1000 zoides each (c.f. above) per liter of an aqueous medium will kill 1,000,000 dinoflagellates per liter within three days. However, in order to obtain a rapid and efficient killing effect, 1,000,000 parasites per liter of aqueous medium seems to be more appropriate. The cascade effect caused by the short generation time of the parasite and the high reproduction rate is strongly enhancing the killing effect within one week so that the major part of the microalgae bloom is killed successively.

Experimental Results

The killing and/or suppressing effect of *Parvilucifera infectans* has been verified in a number of experiments (>20), which all show that the results obtained are reproducible. At all experiments control samples were run simultaneously with samples that were non-infected. The degree of lethal infection after one week incubation was between 90% and 100% for the Dinophysis species *D. acuta, D. norvegica*, and *D. acuminata*, and the Alexandrium species *A. fundyense, A. ostenfeldii, A. tamarense, A. anderssonii, A. cantenella, Gymnodinium sanguineum, Peridinium faeroensis=Pentapharsodinium dalei*. Following species have been found to be infected occasionally in natural samples infected by *Parvilucifera infectans*, viz: *Dinophysis acuta, Dinophysis norvegica, Dinophysis acuminata, Dinophysis caudata, Dinophysis fortii, Dinophysis miles, Dinophysis mitra, Dinophysis rotundata, Dinophysis sacculus, Dinophysis tripos, Alexandrium fundyense, Alexandrium ostenfeldii, Alexandrium tamarense, Alexandrium acatenella, Alexandrium catenella, Alexandrium angustitabulatum, Alexandrium cohorticula, Alexandrium hiranoi Alexandrium minutum, Alexandrium monilatum, Alexandrium tamiyavanchi, Pyrodinium bahamense, Pyrodinium bahamense* var. *compressum, Gambierdiscus toxicus, Ostreopsis lentcularis, Ostreopsis siamensis, Ceratium furca, Ceratium tripos, Ceratium fusus, Ceratium macroceros*, Ceratium sp., Diplopsalis sp., *Protoperidinium crassipes, Protoperidiniun brevipes, Protoperidinium curtipes, Protoperidinium depressum, Protoperidinium bipes*, Protoperidinium sp., *Prorocentrum micans, Prorocentrum lima, Prorocentrum concavum, Prorocentrum mexicanum, Prorocentrum minimum*, Prorocentrum sp., *Gymnodinium breve, Gymnodinium mikimotoi, Gymnodinium catenatum*, Gymnodinium sp., *Peridinium polonicum, Pfiesteria piscicida* and Gyrodinium sp.

According to the experimental results a wide range of the thecate dinoflagellates is infected by *Parvilucifera infectans* and it is thereby concluded that other related species not present in those investigations are infected by *Parvilucifera infectans*, as well, such as the tropic and temperate variants and species.

What is claimed is:

1. Isolated *Parvilucifera infectans*, a new parasitic organism deposited at CCAP under deposition number CCAP 260/1, which is a parasitic flagellate capable of killing toxic microalgae.

2. A Method for eliminating or suppressing algal bloom caused by thecate dinoflagellates wherein *Parvilucifera infectans* identified at CCAP under deposition number CCAP 2060/1, is distributed in a water comprising one or more of said algae.

3. The Method according to claim 2, wherein *Parvilucifera infectans* is distributed in a water comprising one or more of the following species: *Dinophysis acuta, Dinophysis norvegica, Dinophysis acuminata, Dinophysis caudata, Dinophysis fortii, Dinophysis miles, Dinophysis mitra, Dinophysis rotundata, Dinophysis sacculus, Dinophysis tripos, Alexandrium fundyense, Alexandrium ostenfeldii, Alexandrium tamarense, Alexandrium acatenella, Alexandrium catenella, Alexandrium angustitabulatum, Alexandrium cohorticula, Alexandrium hiranoi, Alexandrium minitum, Alexandrium monilatum, Alexandrium tamiyavanichi, Pyrodinium bahamense, Pyrodinium bahamense* var. *compressum, Gambierdiscus toxicus, Ostreopsis lenticularis, Ostreopsis siamensis, Ceratium furca, Ceratium tripos, Ceratium fusus, Ceratium macroceros*, Ceratium sp., Diplopsalis spp, *Protoperidinium crassipes, Protoperidinium brevipes, Protoperidinium curtipes, Protoperidinium depressum, Protoperidinium bipes*, Protoperidinium sp., *Prorocentrum micans, Prorocentrum lima, Prorocentrum concavum, Prorocentrum mexicanum, Prorocentrum minimum*, Prorocentrum sp., *Gymnodinium breve, Gymnodinium mikimotoi, Gymnodinium catenatum*, Gymnodinium sp., *Peridinium polonicum, Pfiesteria pisccida* and Cyrodinium sp.

4. The Method according to claim 2, wherein an aqueous solution comprising *Parvilucifera infectans* sporangia are distributed, whereby the concentration of sporangium in said solution is at least 1000 sporangia per liter.

5. The Method according to claim 2, wherein the *Parvilucifera infectans* is present in a sporangium stage.

6. The Method according to claim 2, wherein the *Parvilucifera infectans* is present in a zoide stage.

7. A Method for propagating *Parvilucifera infectans*, identified at CCAP under deposition number CCAP 2060/1, characterized in that *Parvilucifera infectans* is cultured in a medium containing thioglycollate.

8. A Method for propagating *Parvilucifera infectans*, identified at CCAP under deposition number CCAP 2060/1, characterized in that *Parvilucifera infectans* are added to a monoculture of a dinoflagellate being susceptible to infection by *Parvilucifera infectans*, maintaining the dinoflagellate culture at optimum conditions above 15° C., collecting dead and infected dinoflagellates, and storing said infected material in an aqueous solution or optionally subjecting it to lyophilisation.

9. The Method according to claim 8, wherein the *Parvilucifera infectans* is stored at +5° C. and in darkness.

10. A Method for propagating *Parvilucifera infectans*, identified at CCAP under deposition number CCAP 2060/1, characterized in that *Parvilucifera infectans* are added to water containing dinoflagellates susceptible to infection by *Parvilucifera infectans*, maintaining the dinoflagellate culture at optimum conditions above 15° C., collecting dead and infected dinoflagellates, and storing said infected material in an aqueous solution.

\* \* \* \* \*